US012788362B2

(12) United States Patent
Ebbini

(10) Patent No.: US 12,788,362 B2
(45) Date of Patent: Nov. 10, 2026

(54) WEARABLE ULTRASOUND TRANSDUCER DEVICE

(71) Applicant: REGENTS OF THE UNIVERSITY OF MINNESOTA, Minneapolis, MN (US)

(72) Inventor: Emad S. Ebbini, Edina, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/881,592

(22) PCT Filed: Jul. 6, 2023

(86) PCT No.: PCT/US2023/026985
§ 371 (c)(1),
(2) Date: Jan. 6, 2025

(87) PCT Pub. No.: WO2024/010844
PCT Pub. Date: Jan. 11, 2024

(65) Prior Publication Data

US 2025/0312003 A1 Oct. 9, 2025

Related U.S. Application Data

(60) Provisional application No. 63/358,999, filed on Jul. 7, 2022.

(51) Int. Cl.
*A61B 8/00* (2006.01)
*A61N 7/00* (2006.01)

(52) U.S. Cl.
CPC .......... *A61B 8/4236* (2013.01); *A61B 8/4472* (2013.01); *A61B 8/4494* (2013.01);
(Continued)

(58) Field of Classification Search
CPC ... A61B 8/4236; A61B 8/4472; A61B 8/4494; A61B 8/54; A61B 8/56;
(Continued)

(56) References Cited

U.S. PATENT DOCUMENTS

| | | | |
|---|---|---|---|
| 8,241,217 | B2 | 8/2012 | Chiang et al. |
| 2005/0131296 | A1 | 6/2005 | Chou et al. |

(Continued)

FOREIGN PATENT DOCUMENTS

| | | | |
|---|---|---|---|
| WO | WO 2020/077275 | A1 | 4/2020 |

OTHER PUBLICATIONS

PCT Patent Application No. PCT/US2023/026985, filed Jul. 6, 2023; International Search Report and Written Opinion issued Oct. 12, 2023; 10 pages.

(Continued)

*Primary Examiner* — Adil Partap S Virk
(74) *Attorney, Agent, or Firm* — Mueting Raasch Group

(57) ABSTRACT

A wearable ultrasound transducer device comprises an array of ultrasound transducers (UST array) configured for full-duplex transmit-receive operation. The UST array is supported by a substrate configured for affixation to a body part of a wearer of the device. A controller is operatively coupled to the UST array via a plurality of channel connectors. Each channel connector is coupled to at least one ultrasound transducer of the UST array to define a plurality of channels. A multiplexer is operatively coupled to the channel connectors and the controller. The multiplexer is configured to selectively increase and decrease a number of channels enabled for operation. An input/output (I/O) coupler is operatively coupled to the multiplexer and configured to communicatively couple to, and uncouple from, an imaging
(Continued)

console coupler. A portable power source supplies power to the device at least while the I/O coupler is uncoupled from the imaging console coupler.

20 Claims, 7 Drawing Sheets

(52) U.S. Cl.
CPC .................. *A61B 8/54* (2013.01); *A61B 8/56* (2013.01); *A61N 7/00* (2013.01); *A61B 2560/0214* (2013.01); *A61B 2562/046* (2013.01); *A61B 2562/164* (2013.01); *A61B 2562/227* (2013.01); *A61N 2007/0026* (2013.01); *A61N 2007/0052* (2013.01)

(58) Field of Classification Search
CPC ...... A61B 2560/0214; A61B 2562/046; A61B 2562/164; A61B 2562/227; A61B 8/4227; A61N 7/00; A61N 2007/0026; A61N 2007/0052; A61N 2007/0078
See application file for complete search history.

(56) References Cited

U.S. PATENT DOCUMENTS

| | | | | |
|---|---|---|---|---|
| 2005/0251035 | A1* | 11/2005 | Wong | A61B 8/00 600/459 |
| 2008/0294046 | A1* | 11/2008 | Chiang | G01S 7/5208 600/447 |
| 2010/0240991 | A1* | 9/2010 | Bartlett | A61B 5/0002 709/228 |
| 2010/0331689 | A1* | 12/2010 | Wegener | G01S 7/52034 600/443 |
| 2011/0218423 | A1 | 9/2011 | Hsieh et al. | |
| 2012/0010508 | A1 | 1/2012 | Sokulin et al. | |
| 2012/0197127 | A1* | 8/2012 | Nakamura | G01S 7/52025 600/447 |
| 2012/0203105 | A1* | 8/2012 | Yamamoto | A61B 8/56 600/443 |
| 2012/0283502 | A1 | 11/2012 | Mishelevich | |
| 2016/0038770 | A1 | 2/2016 | Tyler et al. | |
| 2016/0136462 | A1 | 5/2016 | Lewis et al. | |
| 2016/0317125 | A1* | 11/2016 | Arai | A61B 8/0841 |
| 2017/0100092 | A1* | 4/2017 | Kruse | G01S 7/5202 |
| 2019/0254627 | A1 | 8/2019 | Corbett et al. | |
| 2019/0308036 | A1* | 10/2019 | Ebbini | A61B 8/4236 |
| 2020/0275909 | A1* | 9/2020 | Mniece | A61B 8/445 |
| 2021/0293952 | A1* | 9/2021 | Haque | G01H 3/125 |
| 2022/0054026 | A1* | 2/2022 | Slack | A61B 5/02055 |
| 2022/0110611 | A1* | 4/2022 | Adachi | A61B 8/4444 |

OTHER PUBLICATIONS

PCT Patent Application No. PCT/US2023/026985, filed Jul. 6, 2023; International Preliminary Report on Patentability] issued Oct. 12, 2023; 8 pages.

Di Biase et al., Transcranial Focused Ultrasound (tFUS) and Transcranial Unfocused Ultrasound (tUS) Neuromodulation: From Theoretical Principles to Stimulation Practices. *Front Neurol* 10, 549 (2019).

Ebbini et al., Real-time Ultrasound Thermography and Thermometry. *IEEE Signal Process Mag* 35, 166-174 (2018).

Legon et al., Transcranial focused ultrasound neuromodulation of the human primary motor cortex. *Sci Rep* 8, 10007 (2018).

Lewis et al., Design and evaluation of a wearable self-applied therapeutic ultrasound device for chronic myofascial pain. *Ultrasound Med Biol* 39, 1429-1439 (2013).

Lu et al., Transcranial Focused Ultrasound for Noninvasive Neuromodulation of the Visual Cortex. *IEEE Trans Ultrason Ferroelectr Freq Control* 68, 21-28 (2021).

Mueller et al., Transcranial focused ultrasound modulates intrinsic and evoked EEG dynamics. *Brain Stimul* 7, 900-908 (2014).

Protopappas et al., An ultrasound wearable system for the monitoring and acceleration of fracture healing in long bones. *IEEE Trans Biomed Eng* 52, 1597-1608 (2005).

Weng et al., Implementation of a Wearable Ultrasound Device for the Overnight Monitoring of Tongue Base Deformation during Obstructive Sleep Apnea Events. *Ultrasound Med Biol* 43, 1639-1650 (2017).

* cited by examiner

WEARABLE ULTRASOUND TRANSDUCER DEVICE

CROSS-REFERENCE TO RELATED APPLICATION

This application is the § 371 U.S. National Stage of International Application No. PCT/US2023/026985, filed Jul. 6, 2023, which claims the benefit of U.S. Provisional Patent Application No. 63/358,999, filed Jul. 7, 2022, the disclosures of which are incorporated herein by reference in their entireties.

GOVERNMENT FUNDING

This invention was made with government support under NS098781 and NS118785 awarded by National Institutes of Health. The government has certain rights in the invention.

FIELD OF THE DISCLOSURE

The present disclosure relates to ultrasound transducer devices. In particular, the present disclosure relates to ultrasound transducer devices for sensing, imaging, and therapy.

SUMMARY

Embodiments are directed to a wearable ultrasound transducer device comprising an array of ultrasound transducers (UST array) configured for full-duplex transmit-receive operation. The UST array is supported by a substrate configured for affixation to a body part of a wearer of the device. A controller is operatively coupled to the UST array via a plurality of channel connectors. Each of the channel connectors is coupled to at least one ultrasound transducer of the UST array to define a plurality of channels. A multiplexer is operatively coupled to the plurality of channel connectors and the controller. The multiplexer is configured to selectively increase and decrease a number of channels enabled for operation. An input/output (I/O) coupler is operatively coupled to the multiplexer and configured to communicatively couple to, and uncouple from, an imaging console coupler. A portable power source is arranged to supply power to the device at least while the I/O coupler is uncoupled from the imaging console coupler.

Embodiments are directed to a method of operating a wearable ultrasound transducer device. The method involves selectively powering the wearable ultrasound transducer device using a portable power source of the device and a building power source, the device comprising an UST array configured for full-duplex transmit-receive operation and an input/output coupler configured to detachably couple to an imaging console coupler. The method also involves operating, using the portable power source, the device in an ambulatory mode during which the I/O coupler is uncoupled from the imaging console coupler and the UST array is operated in one or both of a sensing mode and a neurostimulation delivery mode. The method further involves operating, using a power supply of the imaging console, the device in a console imaging mode during which the I/O coupler is coupled to the imaging console coupler and the UST array is operated in one or both of an imaging mode and the neurostimulation delivery mode.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
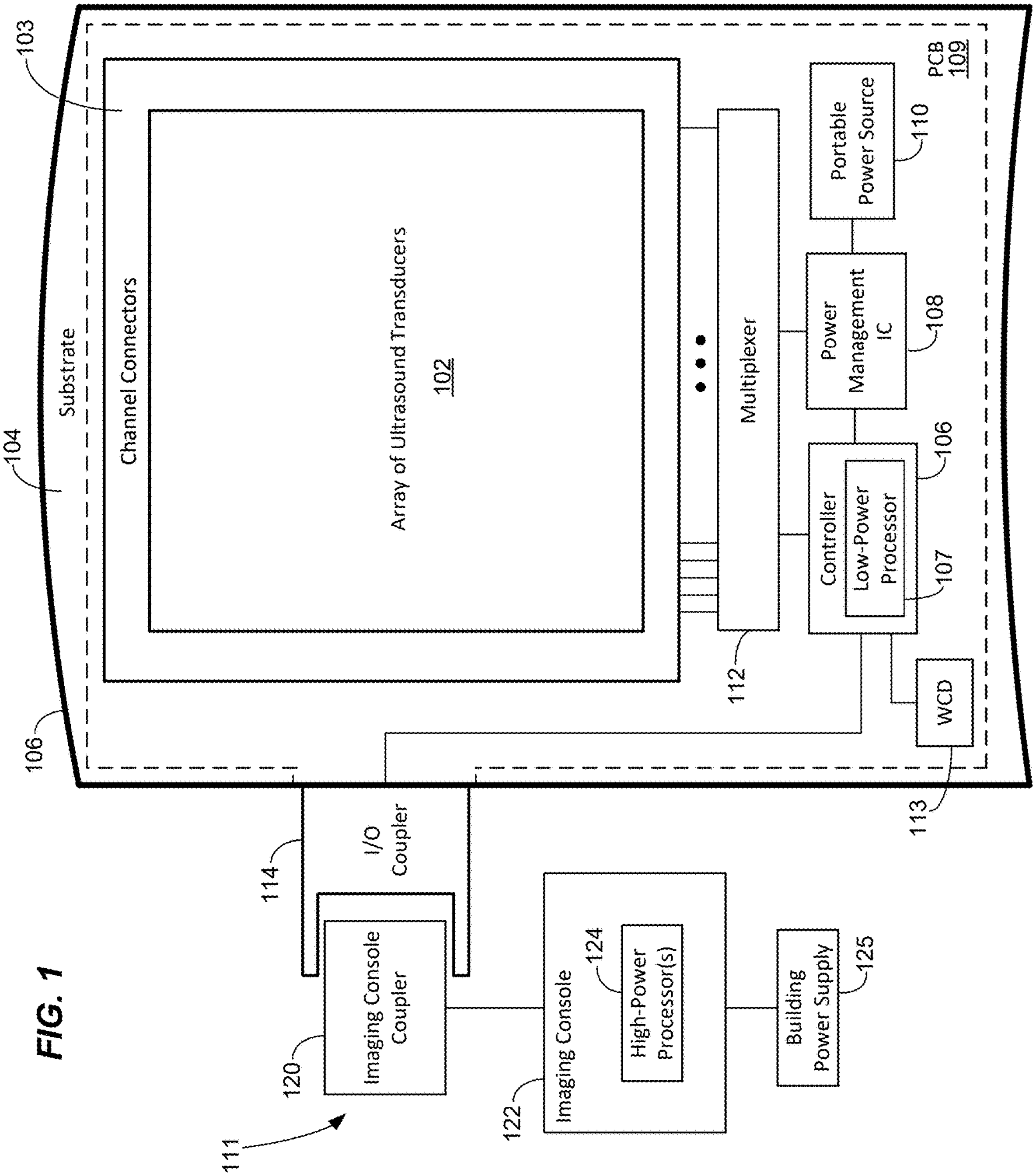
FIG. 1 illustrates a wearable ultrasound transducer device in accordance with any of the embodiments disclosed herein.

Embodiments of the disclosure are directed to wearable ultrasound transducer devices and systems. Wearable ultrasound transducer (WUT) devices of the disclosure can be selectively configured for operation in an ambulatory mode and in a clinical mode involving use of an imaging console system. WUT devices of the disclosure can be configured for sensing, imaging, and/or therapy delivery in both ambulatory and console imaging modes.

In an ambulatory mode (also referred to herein as a sensor mode), a WUT device allows the wearer of the device to roam freely while monitoring targets of interest, e.g., vessel pulsation, tissue stiffness, and thermal properties. While the wearer roams freely, the WUT device can deliver therapy (e.g., neurostimulation therapy) to target tissue of the wearer's body. In a console imaging mode, the same WUT device can be used for more accurate anatomical imaging and validation of sensor measurements made during ambulatory operation under controlled conditions.

Presently available electronics can be used to enable switching interconnections of the WUT device between ambulatory and console imaging modes. In an ambulatory mode of operation, multiplexing technology is used to reduce the ultrasound transducer channel count and low-power drivers are used to support free-roaming, active wearers of the device. In a console imaging mode, light-weight interconnections allow connection to an imaging console without burdening the device wearer.

Advantageously, the WUT device remains positioned in the exact same body location in both the ambulatory and console imaging modes. Maintaining position of the WUT device in both modes eliminates the need to refocus the ultrasound transducers to sense, image, and/or deliver therapy to specified target tissue, which would otherwise be required when using two different ultrasound transducer devices (e.g., a patch device and a clinical ultrasound imaging system).

Ultrasound imaging provides a wealth of information about tissue function if properly used and interpreted. New technologies are allowing for more portable transducers with increasing imaging capabilities. However, present capabilities have not been used with wearable array transducers in either imaging or sensing modes. The present disclosure is directed to use of integrated sensing and imaging technologies utilizing the same wearable ultrasound transducer arrays. WUT devices of the present disclosure can be beneficial for patients with vascular, neurovascular, and neurological disorders. WUT devices can also be used in training athletes and in rehabilitation of patients with muscular disease.

Embodiments of the disclosure are defined in the claims. However, below there is provided a non-exhaustive listing of non-limiting examples. Any one or more of the features of these examples may be combined with any one or more features of another example, embodiment, or aspect described herein.

Example Ex1. A wearable ultrasound transducer device comprises an array of ultrasound transducers (UST array) configured for full-duplex transmit-receive operation, the UST array supported by a substrate configured for affixation to a body part of a wearer of the device. A controller is operatively coupled to the UST array via a plurality of channel connectors, each of the channel connectors coupled to at least one ultrasound transducer of the UST array to define a plurality of channels. A multiplexer is operatively coupled to the plurality of channel connectors and the controller, the multiplexer configured to selectively increase and decrease a number of channels enabled for operation. An input/output (I/O) coupler is operatively coupled to the multiplexer and configured to communicatively couple to, and uncouple from, an imaging console coupler, and a portable power source arranged to supply power to the device at least while the I/O coupler is uncoupled from the imaging console coupler.

Example Ex2. The device according to Ex1, wherein the portable power source is disabled while the I/O coupler is coupled to the imaging console coupler, and a power supply of the imaging console is arranged to supply power to the device while the I/O coupler is coupled to the imaging console coupler.

Example Ex3. The device according to Ex1 or Ex2, wherein the controller is configured to cause the multiplexer to decrease the number of channels for operation in response to the I/O coupler being uncoupled from the imaging console coupler, and increase the number of channels for operation in response to the I/O coupler being coupled to the imaging console coupler.

Example Ex4. The device according to one or more of Ex1 to Ex3, wherein the controller is configured to cause the multiplexer to enable all channels for operation in an imaging mode in response to the I/O coupler being coupled to the imaging console coupler, and disable at least some of the channels for operation in an ambulatory mode in response to the I/O coupler being uncoupled from the imaging console coupler.

Example Ex5. The device according to one or more of Ex1 to Ex4, wherein the controller is configured to cause the multiplexer to enable a first set of the channels for operation in a first mode during which the I/O coupler is uncoupled from the imaging console coupler, and enable a second set of the channels for operation in a second mode during which the I/O coupler is coupled to the imaging console coupler, wherein the number of the channels of the second set exceeds the number of channels of the first set.

Example Ex6. The device according to Ex5, wherein a magnitude of a difference between the number of the channels of the second set relative to the number of channels of the first set is indicative of a magnitude of relative movement between the UST array and target tissue of the body part.

Example Ex7. The device according to Ex5, wherein the number of the channels of the second set exceeds the number of channels of the first set by a factor of about 32 to about 64.

Example Ex8. The device according to Ex5, wherein the number of the channels of the second set exceeds the number of channels of the first set by a factor of about 8 to about 16.

Example Ex9. The device according to Ex5, wherein the number of the channels of the second set exceeds the number of channels of the first set by a factor of about 16 to about 32.

Example Ex10. The device according to one or more of Ex1 to Ex9, wherein the device is configured to operate in an ambulatory mode during which the I/O coupler is uncoupled from the imaging console coupler and the UST array is configured to monitor target tissue of the body part.

Example Ex11. The device according to one or more of Ex1 to Ex10, wherein the device is configured to operate in an ambulatory neurostimulation mode during which the I/O coupler is uncoupled from the imaging console coupler and the UST array is configured to deliver neurostimulation therapy to target tissue of the body part.

Example Ex12. The device according to one or more of Ex1 to Ex11, wherein the substrate comprises or supports a flexible printed circuit board, and the UST array is configured as a conformable, wearable patch.

Example Ex13. The device according to one or more of Ex1 to Ex12, wherein the controller comprises a plurality of circulators each operatively coupled to a transmit circuit, a receive circuit, and one or more ultrasound transducers of the UST array. Each of the circulators comprises a first port configured to receive an excitation waveform from the transmit circuit, a second port configured to provide the excitation waveform to the one or more ultrasound transducers to provide a transmit ultrasound wavefront and receive a reflection waveform from the one or more ultrasound transducers corresponding to a reflection of the transmit ultrasound wavefront during or after providing the excitation waveform, and a third port configured to provide the reflection waveform to the receive circuit during or after receiving the excitation waveform from the transmit circuit.

Example Ex14. The device according to Ex1, comprising a wireless communication device operatively coupled to the controller, the wireless communication device configured to transmit UST array data to an external electronic device.

Example Ex15. The device according to Ex14, wherein the external electronic device comprises one or more of a personal digital assistant, a smartphone, a tablet, a laptop, and a wireless network interface.

Example Ex16. A method comprises selectively powering a wearable ultrasound transducer device using one of a portable power source of the device and an imaging console power source, the device comprising an array of ultrasound transducers (UST array) configured for full-duplex transmit-receive operation and an input/output coupler configured to detachably couple to an imaging console coupler, operating, using the portable power source, the device in an ambulatory mode during which an I/O coupler of the device is uncoupled from the imaging console coupler and the UST array is operated in one or both of a sensing mode and a therapy delivery mode, and operating, using a power supply of the imaging console, the device in a console imaging mode during which the I/O coupler is coupled to the imaging console coupler and the UST array is operated in one or both of an imaging mode and a therapy delivery mode.

Example Ex17. The method according to Ex16, comprising operating the device in the ambulatory mode using a low-power processor of the device, and operating the device in the console imaging mode using a high-power processor of the imaging console.

Example Ex18. The method according to Ex16 or Ex17, comprising decreasing a number of UST array channels for operation in response to the I/O coupler being uncoupled from the imaging console coupler, and increasing the number of UST array channels for operation in response to the I/O coupler being coupled to the imaging console coupler.

Example Ex19. The method according to one or more of Ex16 to Ex18, comprising enabling all UST array channels for operation in the console imaging mode in response to the I/O coupler being coupled to the imaging console coupler, and disabling at least some of the UST array channels for operation in the ambulatory mode in response to the I/O coupler being uncoupled from the imaging console coupler.

Example Ex20. The method according to one or more of Ex16 to Ex19, comprising enabling a first set of UST array channels for operation in a first mode during which the I/O coupler is uncoupled from the imaging console coupler, and enabling a second set of UST array channels for operation in a second mode during which the I/O coupler is coupled to the imaging console coupler, wherein the number of the UST array channels of the second set exceeds the number of channels of the first set.

Example Ex21. The method according to Ex20, wherein the number of the UST array channels of the second set exceeds the number of channels of the first set by a factor of about 8 to about 64.

Figure 2:
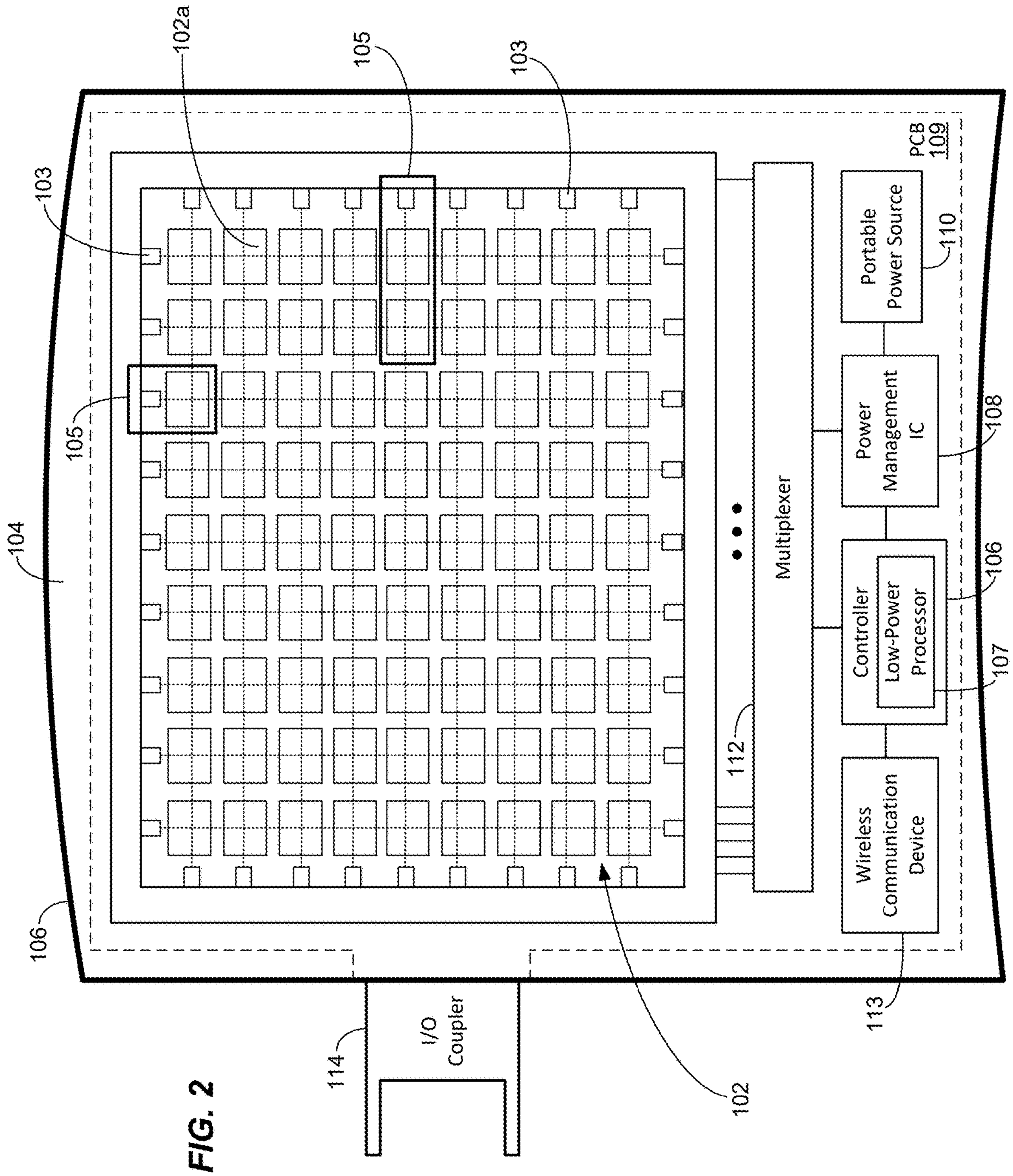
FIG. 2 illustrates a wearable ultrasound transducer device in accordance with any of the embodiments disclosed herein.

FIGS. 1 and 2 illustrate a wearable ultrasound transducer device in accordance with any of the embodiments disclosed herein. FIG. 1 shows a WUT device 100 connected to an imaging console system 111 and configured for operation in a console imaging mode. It is understood that the wearer of the WUT device 100 is typically in a clinic where the imaging console system 111 is located when the WUT device 100 is operated in the console imaging mode. FIG. 2 shows the WUT device 100 disconnected from the imaging console system 111 and configured for operation in an ambulatory mode. It is understood that the wearer of the WUT device 100 can be freely roaming and need not be at the clinic when the WUT device 100 is operated in the ambulatory mode.

The WUT device 100 shown in FIGS. 1 and 2 includes a substrate 104 which incorporates or supports a printed circuit board (PCB) 109. Preferably, the substrate 104 and the PCB 109 are flexible, allowing the WUT device 100 to conform to the shape of a specified body part (e.g., skull, throat, abdomen, leg). As such, the WUT device 100 can be configured for affixation to any body part of a wearer of the device 100. It is understood that some or all of the substrate 104 and the PCB 109 can be rigid in some implementations.

The WUT device 100 also includes an array of ultrasound transducers 102 supported by the substrate 104. The transducers of the UST array 102 and other electrical and/or electronic components of the WUT device 100 are respectively connected to, and interconnected by, the PCB 109. According to any of the embodiments disclosed herein, the UST array 102 can be configured for full-duplex transmit-receive operation.

The WUT device 100 includes a controller 106 operatively coupled to the UST array 102 via a plurality of channel connectors 103. Each of the channel connectors 103 is coupled to at least one UST transducer **102*a* to define a plurality of channels 105. In some implementations, and as shown in in FIG. 2, each channel can comprise one channel connector 103 and a single UST transducer 102*a*. In other implementations, each channel can comprise one channel connector 103 and a multiplicity of UST transducers 102*a* (e.g., two, three or more UST transducers 102*a*). The number of UST transducers 102*a* per channel 105 can be the same or differ in a particular WUT device 100**.

A multiplexer 112 is operatively coupled to the plurality of channel connectors 103 and the controller 106. The multiplexer 112, in response to control signals produced by the controller 106, is configured to selectively increase and decrease a number of channels 105 enabled for operation at any given time. The controller 106 is configured to cause the multiplexer 112 to increase or decrease the number of channels 105 enabled for operation depending on the selected mode of operation (e.g., ambulatory mode, console imaging mode), as will be described hereinbelow.

The WUT device 100 further includes an input/output (I/O) coupler 114 which is operatively coupled to the multiplexer 112. The I/O coupler 114 is configured to communicatively coupled to, and uncouple from, a coupler 120 of an imaging console 122. In an ambulatory mode of operation, for example, the I/O coupler 114 is physically and communicatively uncoupled from the imaging console coupler 120. In a console imaging mode of operation, the I/O coupler 114 is physically and communicatively coupled to the imaging console coupler 120.

The WUT device 100 also includes a portable power source 110 and a power management IC (e.g., a PMIC) 108 which cooperate to provide power to the various power-consuming components of the WUT device 100. The portable power source 110 can include a rechargeable battery, such as a lithium-ion battery. The power management IC 108 is a solid-state device that controls the flow and direction of electrical power through the WUT device 100. The power management IC 108 can include multiple system rails and provides a number of functions including, for example, DC-to-DC conversion, charging of the portable power source 110, power-source selection, voltage scaling, voltage regulation, and power sequencing, among other functions.

The WUT device 100 can also include a wireless communication device 113 configured to communicate with an external electronic device. For example, the external electronic device can include one or more of a personal digital assistant, a smartphone, a tablet, a laptop, and a wireless network interface. Data acquired by the WUT device 100 can be communicated wirelessly to the external electronic device, such as via a paired (e.g., encrypted) communication channel established between the WUT device 100 and the external electronic device. Data can be transferred from the external electronic device to the WUT device 100 via the wireless communication device 113, such as for querying/interrogating the WUT device 100 and/or updating firmware, for example.

FIG. 1 further shows the WUT device 100 operatively coupled to the imaging console system 111 which includes the imaging console coupler 120 operatively coupled to the imaging console 122. At the clinic, and without removing the WUT device 100 from the wearer's body, the I/O coupler 114 of the WUT device 100 can be communicatively coupled to the imaging console coupler 120 of the imaging console 122. The WUT device 100 can then be operated in the console imaging mode.

In the console imaging mode, primary control of the WUT device 100 is taken over by one or more high-power processors 124 of the imaging console 122. The processors 124 of the imaging console 122 can cooperate with the processor 107 (e.g., low-power processor relative to the imaging console processor(s)) of the WUT device controller 106 to conduct more accurate anatomical imaging (and under controlled conditions) than is possible when operating in the ambulatory mode. In the console imaging mode, the low-power processor 107 of the WUT controller 106 can serve as a slave to the high-power processor(s) 124 of the imaging console 122.

In some implementations, the portable power source 110 is disabled by the power management IC 108 when the I/O coupler 114 is coupled to the imaging console coupler 120. A power supply 125 (e.g., a 120V AC wall outlet) of the imaging console 122 is arranged to supply power to the WUT device 100 while the I/O coupler 114 is coupled to the imaging console coupler 120. It is understood that the imaging console 122 can draw power from a building power supply 125 and, as such, is not limited in terms of power consumption or utilization.

According to various implementations, the processor 107 of the WUT controller 106 can be representative of any combination of one or more logic devices (e.g., multi-core processor, digital signal processor (DSP), microprocessor, programmable controller, general-purpose processor, special-purpose processor, hardware controller, software controller, a combined hardware and software device) and/or other digital logic circuitry (e.g., ASICs, FPGAs), and software/firmware configured to implement the functionality disclosed herein. The controller 106 can incorporate or be coupled to various analog components (e.g., analog front-end), ADC and DAC components, and filters. The processor 107 can be coupled to, or incorporate, memory. The memory can include one or more types of memory, including ROM, RAM, SDRAM, NVRAM, EEPROM, and FLASH, for example. The memory can be configured to store measurements and data acquired by the processor 107 during ambulatory operation of the WUT device 100.

Figure 3:
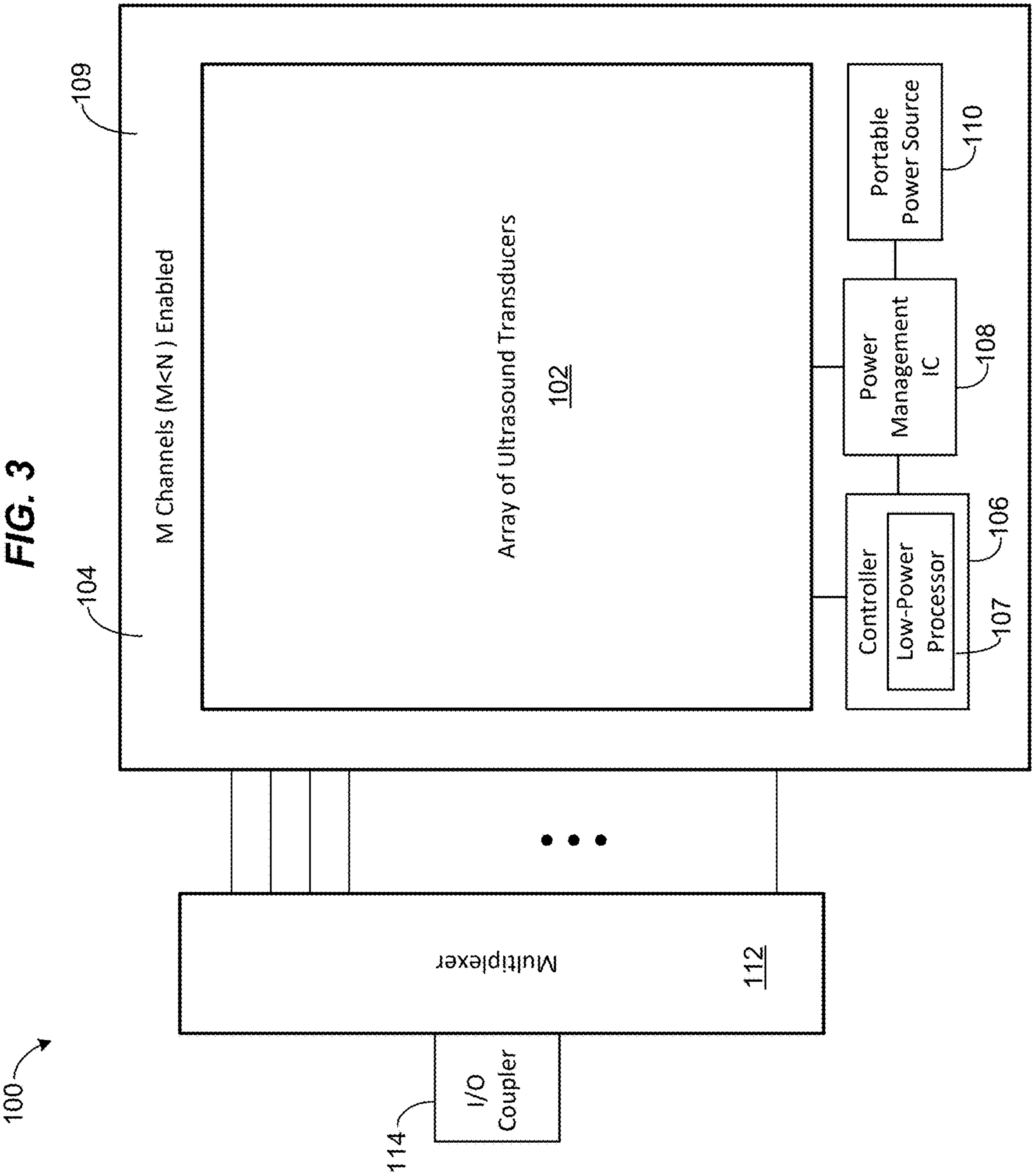
FIG. 3 illustrates a wearable ultrasound transducer device in accordance with any of the embodiments disclosed herein.
Figure 4:
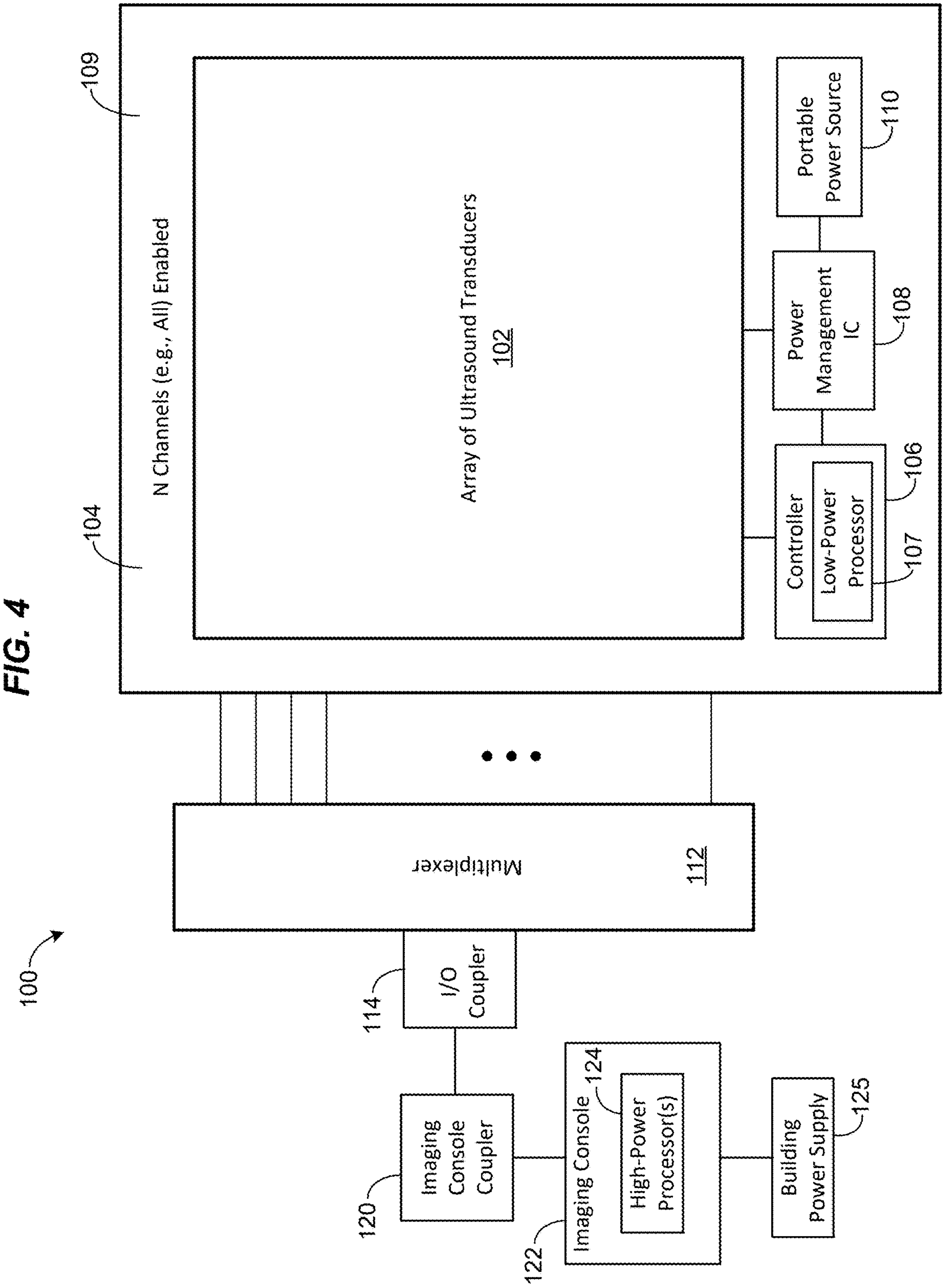
FIG. 4 illustrates a wearable ultrasound transducer device in accordance with any of the embodiments disclosed herein.

FIGS. 3 and 4 show high-level views of a WUT device 100 in an ambulatory mode of operation (FIG. 3) and a console imaging mode of operation (FIG. 4), respectively. As discussed previously, the controller 106 is configured to cause the multiplexer 112 to selectively decrease and increase the number of UST array channels 105 depending on the particular mode of WUT device operation.

In FIG. 3, the WUT device 100 is shown operating in an ambulatory mode, in which the I/O coupler 114 is decoupled from the imaging console coupler 120. The controller 106 is configured to decrease the number of UST array channels 105 for operation in response to the I/O coupler 114 being uncoupled from the imaging console coupler 120. For example, when operating in an ambulatory mode, the controller 106 causes the multiplexer 112 to decrease (e.g., disable) the number of UST array channels 105 from a maximum number of available UST array channels 105 (e.g., all channels) to N channels, where N is an integer less (e.g., significantly less) than the maximum number of available UST array channels 105. When operating in a console imaging mode, as is shown in FIG. 4, the controller 106 causes the multiplexer 112 to increase (e.g., enable) the number of UST array channels 105 to a number greater than that associated with the ambulatory mode (e.g., the maximum number of available UST array channels 105).

In general, the number of UST array channels 105 enabled by the controller 106 during an ambulatory mode of operation is dependent in large part on the type of body part to which the WUT device 100 is affixed. More particularly, the magnitude of relative movement between the WUT device 100 and the body part to which it is affixed can dictate the number of UST array channels 105 that need to be enabled by the controller 106 during ambulatory operation.

For example, fewer UST array channels 105 are enabled during ambulatory operation where the magnitude of relative movement between the WUT device 100 and a particular body part is relatively low. Such body parts associated with low relative movement include the skull/brain and thoracic arterial target tissue. A greater number of UST array channels 105 are enabled during ambulatory operation where the magnitude of relative movement between the WUT device 100 and a particular body part is relatively high. Such body parts associated with relatively high relative movement include the abdomen and legs.

The WUT device 100 can be configured to have a specified number of UST array channels 105. The UST array channels 105 may be arranged in terms of sets of UST array channels 105, with each set corresponding to a specified number of individual UST array channels 105. The controller 106 can be configured to cause the multiplexer 112 to enable a first set of the UST array channels 105 for operation in an ambulatory mode during which the I/O coupler 114 is uncoupled from the imaging console coupler 120. When operating in a console imaging mode, the controller 106 can be configured to cause the multiplexer 112 to enable a second set of UST array channels 105 for operation during which the I/O coupler 114 is coupled to the imaging console coupler 120. The magnitude of the difference between the number of the UST array channels 105 of the second set relative to the number of UST array channels 105 of the first set is indicative of a magnitude of relative movement between the UST array 102 and target tissue of the body part.

For low-movement target tissue, the number of UST array channels 105 of the second set can exceed the number of UST array channels 105 of the first set by a factor of about 32 to about 64. For high-movement target tissue, the number of UST array channels 105 of the second set can exceed the number of channels 105 of the first set by a factor of about 8 to about 16. For moderate-movement target tissue, the number of UST array channels 105 of the second set can exceed the number of UST array channels 105 of the first set by a factor of about 16 to about 32.

For purposes of illustration, and not of limitation, the WUT device 100 can be configured to have 256 UST array channels which can be assigned to a first set and a second set of individual channels 105. When affixed to a relatively low-movement body part (e.g., the skull), the number of UST array channels 105 enabled by the controller 106 during ambulatory operation can be from about 4 to about 8 channels 105. When affixed to a relatively high-movement body part (e.g., the abdomen), the number of UST array channels 105 enabled by the controller 106 during ambulatory operation can be from about 16 to about 32 channels 105. When affixed to a relatively moderate-movement body part (e.g., the chest), the number of UST array channels 105 enabled by the controller 106 during ambulatory operation can be from about 8 to about 16 channels 105.

Figure 5A:
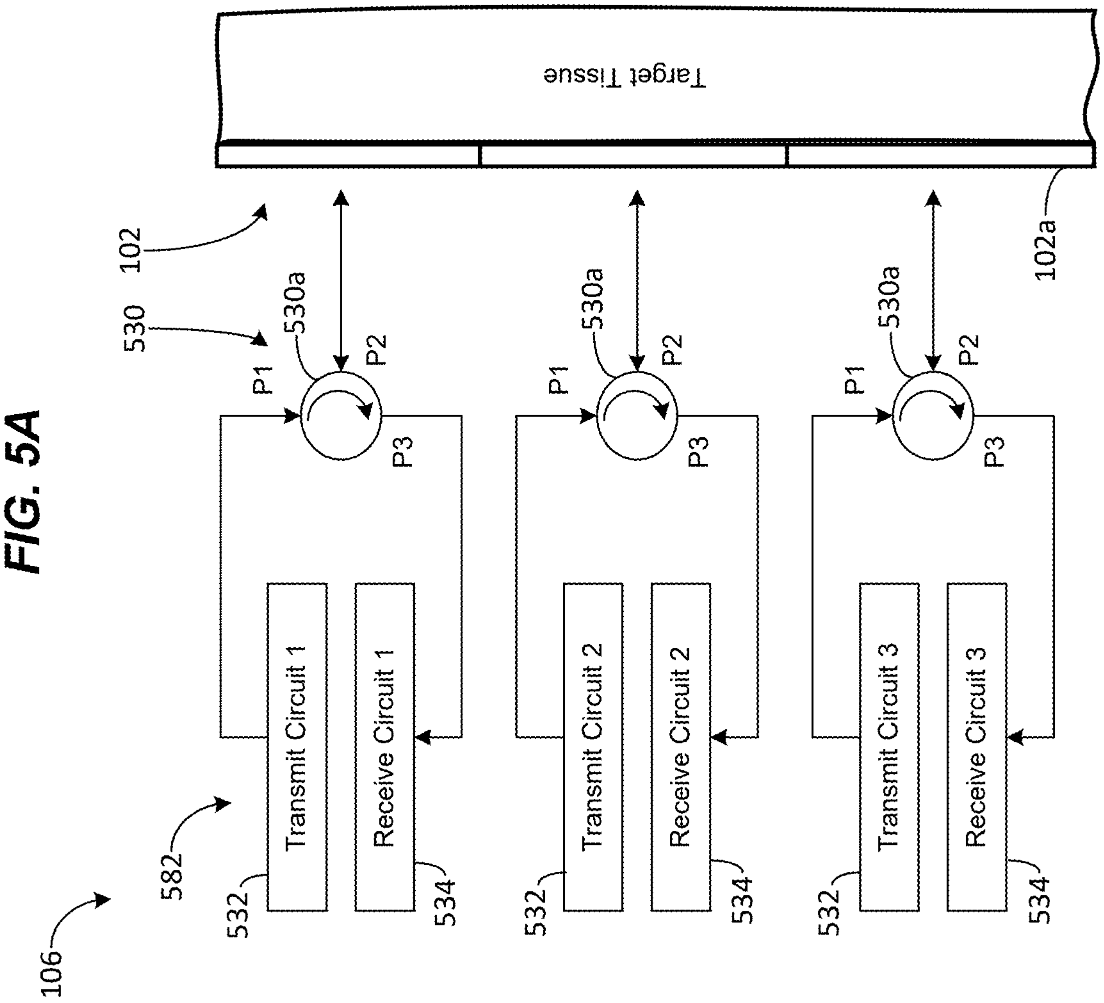
FIG. 5A illustrates components of a controller of a wearable ultrasound transducer device in accordance with any of the embodiments disclosed herein.
Figure 5B:
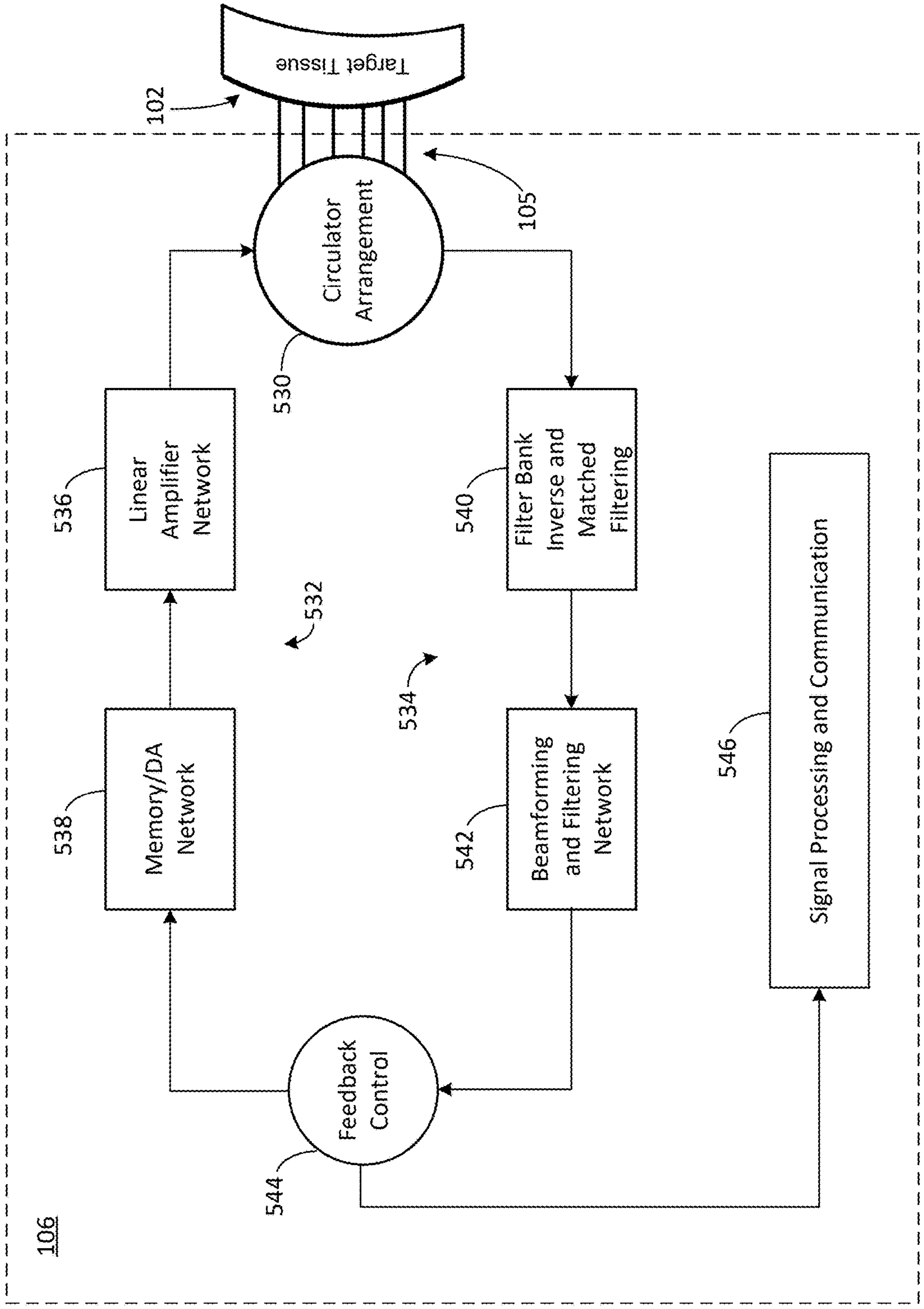
FIG. 5B illustrates components of a controller of a wearable ultrasound transducer device in accordance with any of the embodiments disclosed herein.

FIGS. 5A and 5B illustrate additional components of the controller 106 of a WUT device 100 in accordance with any of the embodiments disclosed herein. As illustrated, the controller 106 can include a circulator arrangement 530. The circulator arrangement 530 can be operably coupled to a transmit circuit 532 and a receive circuit 534. The circulator arrangement 530 can facilitate the ability of the WUT device 100 to provide full-duplex transmit-receive functionality.

As is shown in the FIG. 5A, the controller 106 can comprise a plurality of circulators 530*a* each operatively coupled to a transmit circuit 532, a receive circuit 534, and one or more ultrasound transducers 102*a*. Each of the circulators 530*a* comprises a first port, P1, configured to receive an excitation waveform from the transmit circuit 532. Each circulator 530*a* also comprises a second port, P2, configured to provide the excitation waveform to the ultrasound transducer(s) 102*a* to provide a transmit ultrasound wavefront, and to receive a reflection waveform from the ultrasound transducer(s) corresponding to a reflection of the transmit ultrasound wavefront during or after providing excitation waveform. Each of the circulators 530*a* further comprises a third port, P3, configured to provide the reflection waveform to the receive circuit 534 during or after receiving the excitation waveform from the transmit circuit 532.

Each channel connector 103 (see FIGS. 1 and 2) can be operably coupled to the controller 106 via the multiplexer 112. Each channel connector 103 can be coupled to at least one circulator 530*a*. Each circulator 530*a* can be operably coupled to at least one transmit circuit 532 and at least one receive circuit 534. As illustrated, each circulator 530*a* is operably coupled to one transmit circuit 532 and one receive circuit 534.

The circulator 530*a* can be described as an active circulator. The circulator 530*a* may use a 3-port network, which passes a first signal from Port 1 (driver) to Port 2 (transducer) but rejects the first signal at Port 3 (ADC) and passes a second signal from Port 2 to Port 3 but rejects the second signal at Port 1. This so-called clockwise circulator action uses a design of the feedback network that creates signal cancellation at even numbered stages (i.e., modulo-2, note the 3 stages are tied in a circular pattern). In some embodiments, the circulator 530*a* may use an OpAmp-based topology (e.g., using three operational amplifiers), although any suitable circulator topology can be used.

The circulator 530*a* may include a plurality of ports configured to forward signals received at one port to another port in a "circular" fashion. In the illustrated embodiment, the circulator 530*a* includes a first port (P1), a second port (P2), and a third port (P3). The first port, P1, can be configured to receive an excitation waveform from transmit circuit 532. The second port, P2, can be configured to provide the excitation waveform (received by the first port) to the transducer 102*a* to provide a transmit ultrasound wavefront. The second port, P2, can concurrently be configured to receive a reflection waveform from the transducer 102*a* corresponding to a reflection of the transmit ultrasound wavefront during or after providing the excitation waveform. The third port, P3, can be configured to provide the reflection waveform to receive circuit 534 during or after receiving the excitation waveform from transmit circuit 532. In some implementations, the receive circuit 534 can be configured to begin receiving the reflection waveform from the third port, P3, even while the transmit circuit 532 is providing the transmit excitation waveform to the first port, P1.

Using one or more circulators 530*a*, the controller 106 can be configured to provide a continuous excitation waveform to the transducer 102*a* on each UST array channel 105 even while receiving a continuous reflection waveform on the same channels. As used herein, the term "continuous excitation waveform" refers to a waveform that, in contrast to a series of pulses or bursts, does not use breaks in transmission to detect a reflection waveform.

The controller 106 can be described as having one or more channel interfaces 582. Each channel interface 582 can include one or more transmit circuits 532, one or more receive circuits 534, and one or more circulators 530*a*. As illustrated, each channel interface 582 includes one transmit circuit 532, one receive circuit 534, and one circulator 530*a*. Although only three channel interfaces 582 are shown in FIG. 5A, any number of channel interfaces 582 can be used to provide sensing, imaging and/or therapy using the UST array 102 depending on the particular application.

FIG. 5B illustrates additional components of the controller 106 in accordance with any of the embodiments disclosed herein. In general, a higher signal-to-noise ratio (SNR) for receive circuitry of controller 106 is desirable (e.g., maximizing the SNR of the receiver), which may depend on the performance of the circulator arrangement 530. Receive circuitry can be described as including circulator arrangement 530 and receive circuit 534. In some implementations, field-programmable gate array (FPGA) circuitry with programmable amplifier networks can be used in the receive circuitry to achieve a high SNR.

The transmit circuit 532 can include a memory and digital-to-analog (DA) network 538 and a linear amplifier network 536. The linear amplifier network 536 can include broadband matching network configured to optimize the efficiency of the transmission through the circulator arrangement 530 and UST array 102. The memory and DA network 538 can be configured to store the element waveforms necessary to produce a desired wavefront near the target point(s) while avoiding direct exposure to any critical point(s) defined by the user.

The receive circuit 534 can include a filter bank inverse and matched filtering network 540 and a beamforming and filtering network 542. The filter bank inverse and matched filtering network 540 can be configured to correct for waveform distortion due to propagation in inhomogeneous media (e.g., skull). The beamforming and filtering network 542 can be configured to maximize the SNR from the target point(s) and suppress interference from strongly scattering objects. In some implementations, the linear amplifier network 536 can be operably coupled to the filter bank inverse and matched filtering network 540 to produce synchronized transmission wavefronts for motion tracking, elastography, thermography, and/or other signal processing.

Both the transmit circuit 532 and the receive circuit 534 can be operably coupled to a feedback control 544. The feedback control 544 can be configured to facilitate using different modes of the system, such as an adaptive sensing mode, an adaptive imaging mode, and an adaptive therapy mode. The feedback control 544 can be operably coupled to a signal processing and communication processor 546. The signal processing and communication processor 546 can be configured to produce sensing and imaging data and, for example, transmit data wirelessly to a mobile device as previously discussed. In particular, the signal processing and communication processor 546 can be configured to interpret a reflection waveform from receive circuit 534 for storage or processing. Additional details of the controller 106 can be found in commonly-owned, co-pending US Patent Publication No. 2019/0308036, which is incorporated herein by reference in its entirety.

Figure 6:
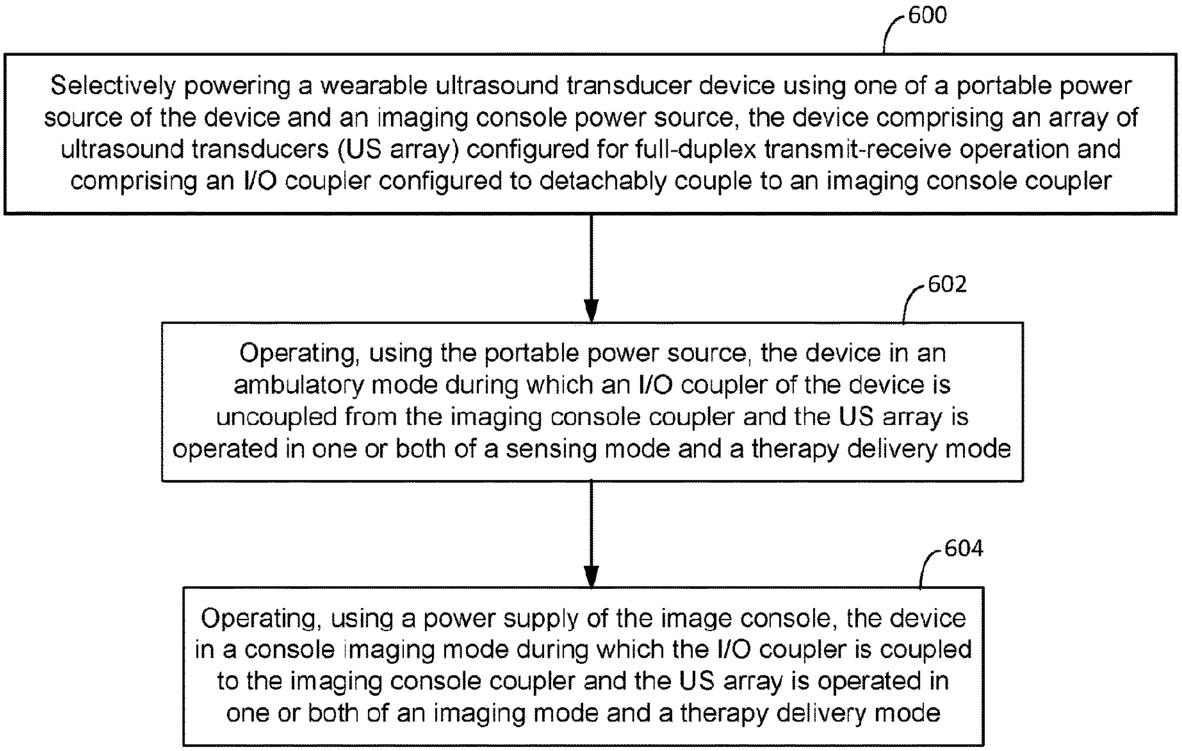
FIG. 6 illustrates a method of operating a wearable ultrasound transducer device in accordance with any of the embodiments disclosed herein.

FIG. 6 illustrates a method of operating a WUT device in accordance with any of the embodiments disclosed herein. The method shown in FIG. 6 can be implemented by the controller 106 shown in other figures, such as by the processor 107 executing program instructions corresponding to the processes shown in FIG. 6. The method involves selectively powering 600 a WUT device using one of a portable power source of the device and an imaging console power source. The WUT device comprises an array of ultrasound transducers configured for full-duplex transmit-receive operation and an input/output coupler configured to detachably coupled to an imaging console coupler.

The method also involves operating 602, using the portable power source, the WUT device in an ambulatory mode during which the I/O coupler is uncoupled from the imaging console coupler in the UST array is operated in one or both of a sensing mode and a therapy delivery (e.g., neurostimulation) mode. In the ambulatory mode of operation, the WUT device operates with a limited (e.g., reduced) number of enabled ultrasound transducers as previously discussed. The method further involves operating 604, using a power supply of the imaging console, the WUT device in a console imaging mode during which the I/O coupler is coupled to the imaging console coupler and the UST array is operated in one or both of an imaging mode and a therapy delivery (e.g., neurostimulation) mode. In the imaging console mode of operation, the WUT device operates with all or nearly all of the ultrasound transducers enabled as previously discussed.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g., 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a radio chip may be operably coupled to an antenna element to provide a radio frequency electric signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. A wearable ultrasound transducer device, comprising:

an array of ultrasound transducers (UST array) configured for full-duplex transmit-receive operation, the UST array supported by a substrate configured for affixation to a body part of a wearer of the device;

a controller operatively coupled to the UST array via a plurality of channel connectors, each of the channel connectors coupled to at least one ultrasound transducer of the UST array to define a plurality of channels;

a multiplexer operatively coupled to the plurality of channel connectors and the controller, the multiplexer configured to selectively increase and decrease a number of channels enabled for operation;

an input/output (I/O) coupler operatively coupled to the multiplexer and configured to communicatively couple to, and uncouple from, an imaging console coupler; and a portable power source arranged to supply power to the device at least while the I/O coupler is uncoupled from the imaging console coupler;

wherein the controller is configured to cause the multiplexer to:

decrease the number of channels for operation in response to the I/O coupler being uncoupled from the imaging console coupler; and increase the number of channels for operation in response to the I/O coupler being coupled to the imaging console coupler.

2. The device according to claim 1, wherein:

the portable power source is disabled while the I/O coupler is coupled to the imaging console coupler; and a power supply of the imaging console is arranged to supply power to the device while the I/O coupler is coupled to the imaging console coupler.

3. The device according to claim 1, wherein the controller is configured to cause the multiplexer to:

enable all channels for operation in an imaging mode in response to the I/O coupler being coupled to the imaging console coupler; and disable at least some of the channels for operation in an ambulatory mode in response to the I/O coupler being uncoupled from the imaging console coupler.

4. The device according to claim 1, wherein the controller is configured to cause the multiplexer to:

enable a first set of the channels for operation in a first mode during which the I/O coupler is uncoupled from the imaging console coupler; and enable a second set of the channels for operation in a second mode during which the I/O coupler is coupled to the imaging console coupler;

wherein the number of the channels of the second set exceeds the number of channels of the first set.

5. The device according to claim 4, wherein a magnitude of a difference between the number of the channels of the second set relative to the number of channels of the first set is indicative of a magnitude of relative movement between the UST array and target tissue of the body part.

6. The device according to claim 4, wherein the number of the channels of the second set exceeds the number of channels of the first set by a factor of 32 to 64.

7. The device according to claim 4, wherein the number of the channels of the second set exceeds the number of channels of the first set by a factor of 8 to 16.

8. The device according to claim 4, wherein the number of the channels of the second set exceeds the number of channels of the first set by a factor of 16 to 32.

9. The device according to claim 1, wherein the device is configured to operate in an ambulatory mode during which the I/O coupler is uncoupled from the imaging console coupler and the UST array is configured to monitor target tissue of the body part.

10. The device according to claim 1, wherein the device is configured to operate in an ambulatory neurostimulation mode during which the I/O coupler is uncoupled from the imaging console coupler and the UST array is configured to deliver neurostimulation therapy to target tissue of the body part.

11. The device according to claim 1, wherein:

the substrate comprises or supports a flexible printed circuit board; and the UST array is configured as a conformable, wearable patch.

12. The device according to claim 1, wherein the controller comprises:

a plurality of circulators each operatively coupled to a transmit circuit, a receive circuit, and one or more ultrasound transducers of the UST array, each of the circulators comprising:

a first port configured to receive an excitation waveform from the transmit circuit;

a second port configured to:

provide the excitation waveform to the one or more ultrasound transducers to provide a transmit ultrasound wavefront, and receive a reflection waveform from the one or more ultrasound transducers corresponding to a reflection of the transmit ultrasound wavefront during or after providing the excitation waveform; and a third port configured to provide the reflection waveform to the receive circuit during or after receiving the excitation waveform from the transmit circuit.

13. The device according to claim 1, comprising a wireless communication device operatively coupled to the controller, the wireless communication device configured to transmit UST array data to an external electronic device.

14. The device according to claim 13, wherein the external electronic device comprises one or more of a personal digital assistant, a smartphone, a tablet, a laptop, and a wireless network interface.

15. A method, comprising:

selectively powering a wearable ultrasound transducer device using one of a portable power source of the device and an imaging console power source, the device comprising an array of ultrasound transducers (UST array) configured for full-duplex transmit-receive operation and an input/output coupler configured to detachably couple to an imaging console coupler;

operating, using the portable power source, the device in an ambulatory mode during which an I/O coupler of the device is uncoupled from the imaging console coupler and the UST array is operated in one or both of a sensing mode and a therapy delivery mode;

operating, using a power supply of the imaging console, the device in a console imaging mode during which the I/O coupler is coupled to the imaging console coupler and the UST array is operated in one or both of an imaging mode and a therapy delivery mode;

decreasing a number of UST array channels for operation in response to the I/O coupler being uncoupled from the imaging console coupler; and increasing the number of UST array channels for operation in response to the I/O coupler being coupled to the imaging console coupler.

16. The method according to claim 15, comprising:

operating the device in the ambulatory mode using a low-power processor of the device; and operating the device in the console imaging mode using a high-power processor of the imaging console.

17. The method according to claim 15, comprising:

enabling all UST array channels for operation in the console imaging mode in response to the I/O coupler being coupled to the imaging console coupler; and disabling at least some of the UST array channels for operation in the ambulatory mode in response to the I/O coupler being uncoupled from the imaging console coupler.

18. The method according to claim 15, comprising:

enabling a first set of UST array channels for operation in a first mode during which the I/O coupler is uncoupled from the imaging console coupler; and enabling a second set of UST array channels for operation in a second mode during which the I/O coupler is coupled to the imaging console coupler;

wherein the number of the UST array channels of the second set exceeds the number of channels of the first set.

19. The method according to claim 18, wherein the number of the UST array channels of the second set exceeds the number of channels of the first set by a factor of 8 to 64.

20. A wearable ultrasound transducer device, comprising:

an array of ultrasound transducers (UST array) configured for full-duplex transmit-receive operation, the UST array supported by a substrate configured for affixation to a body part of a wearer of the device;

a controller operatively coupled to the UST array via a plurality of channel connectors, each of the channel connectors coupled to at least one ultrasound transducer of the UST array to define a plurality of channels;

a multiplexer operatively coupled to the plurality of channel connectors and the controller, the multiplexer configured to selectively increase and decrease a number of channels enabled for operation;

an input/output (I/O) coupler operatively coupled to the multiplexer and configured to communicatively couple to, and uncouple from, an imaging console coupler; and a portable power source arranged to supply power to the device at least while the I/O coupler is uncoupled from the imaging console coupler;

wherein the controller is configured to cause the multiplexer to:

enable a first set of the channels for operation in a first mode during which the I/O coupler is uncoupled from the imaging console coupler; and enable a second set of the channels for operation in a second mode during which the I/O coupler is coupled to the imaging console coupler;

wherein the number of the channels of the second set exceeds the number of channels of the first set.

* * * * *